United States Patent [19]

Kawamura et al.

[11] 4,273,941

[45] * Jun. 16, 1981

[54] PROCESS FOR PRODUCING P-HYDROXYBENZALDEHYDE

[75] Inventors: Masao Kawamura, Akashi; Tadaaki Nishi, Kakogawa; Kunioki Kato, Akashi; Hiroshi Mizokami, Kakogawa; Tadashi Kanazawa, Hyogo, all of Japan

[73] Assignee: Seitetsu Kagaku Co., Ltd., Hyogo, Japan

[ * ] Notice: The portion of the term of this patent subsequent to Mar. 25, 1997, has been disclaimed.

[21] Appl. No.: 55,414

[22] Filed: Jul. 6, 1979

Related U.S. Application Data

[62] Division of Ser. No. 938,125, Aug. 30, 1978, Pat. No. 4,195,041.

[30] Foreign Application Priority Data

| | | |
|---|---|---|
| Sep. 7, 1977 [JP] | Japan | 52-108084 |
| Sep. 7, 1977 [JP] | Japan | 52-108085 |
| Sep. 8, 1977 [JP] | Japan | 52-108552 |
| Oct. 3, 1977 [JP] | Japan | 52-119355 |

[51] Int. Cl.$^3$ .................. C07C 85/11; C07C 89/00
[52] U.S. Cl. ................................... 564/416
[58] Field of Search ............ 260/600 R, 575, 578, 260/580

[56] References Cited

U.S. PATENT DOCUMENTS

| | | | |
|---|---|---|---|
| 1,910,679 | 5/1933 | Crawford | 260/600 R |
| 3,365,500 | 1/1968 | Pontz | 260/600 R |
| 4,195,041 | 3/1980 | Kawamara et al. | 260/580 |

OTHER PUBLICATIONS

Organic Synthesis Collective, vol. 3, (1955), pp. 130–131.
Organic Synthesis, vol. 31, (1951), pp. 6 and 7.

*Primary Examiner*—Winston A. Douglas
*Assistant Examiner*—Y. Harris-Smith
*Attorney, Agent, or Firm*—Jordan and Hamburg

[57] ABSTRACT

A process for producing p-hydroxybenzaldehyde through p-aminobenzaldehyde from p-nitrotoluene, comprising reacting p-nitrotoluene with sodium polysulphide in an alcohol-alkali aqueous solution mixed solvent in the presence or absence of an aprotic polar compound to produce p-aminobenzaldehyde, diazotizing the p-aminobenzaldehyde and then hydrolyzing the diazotized p-aminobenzaldehyde to produce p-hydroxybenzaldehyde.

12 Claims, No Drawings

PROCESS FOR PRODUCING P-HYDROXYBENZALDEHYDE

This is a division of application Ser. No. 938,125, filed Aug. 30, 1978 now U.S. Pat. No. 4,195,041.

This invention relates to a process for producing p-hydroxybenzaldehyde and more particularly it relates to a process for producing p-hydroxybenzaldehyde by reacting p-nitrotoluene with sodium polysulphide to obtain p-aminobenzaldehyde, diazotizing the thus obtained p-aminobenzaldehyde and hydrolyzing the diazotized p-aminobenzaldehyde to produce the p-hydroxybenzaldehyde.

P-hydroxybenzaldehyde is useful as an intermediate material for medicines, agricultural chemicals, perfumery and is in increasing demand year by year. There have heretofore been known many processes such as a Reimer-Tiemann process disclosed in U.S. Pat. No. 3,365,500 and a phosphoric acid ester process described in Japanese Patent Gazette No. 3828/73. The former process comprises reacting phenol with chloroform in the presence of an alkali to produce salicylaldehyde and p-hydroxybenzaldehyde; however, the amount of p-hydroxybenzaldehyde so produced is within the range of as small as 20–25% of the total weight of said two aldehydes and the yield thereof is within the range of 15–20% at highest based on the amount of phenol used because the main product contained in the reaction mixture is salicylaldehyde.

On the other hand, the latter process comprises chlorinating tri-p-cresylphosphate in the presence of an azobis type catalyst such as azobis isobutyronitrile and hydrolyzing the thus chlorinated compound to produce p-hydroxybenzaldehyde; however, this known process is disadvantageous in that tri-p-cresylphosphate as the starting material is an awkward compound to handle industrially because it is solid at ambient temperature and that said chlorinated compound takes a long time to be hydrolyzed because of its low hydrolyzability.

In addition, there have hitherto been known processes for the production of p-aminobenzaldehyde by reacting p-nitrotoluene with sodium polysulphide; for example, Organic Synthesis, Collective, Vol. 4, p. 31 describes a process for the production of p-aminobenzaldehyde by reacting p-nitrotoluene with sodium polysulphide prepared by incorporating sodium sulphide with sulphur and further with sodium hydroxide. However, this known process can only produce p-aminobenzaldehyde in a yield of as low as 40–50%.

Diazotization or diazo-reactions, in general, are illustrated in, for example, Experimental Organic Chemistry (third revised edition) written by S. Yamaguchi and published in 1934 by Nankodo Bookstore, Japan, the publication describing on page 339 thereof a process for the synthesis of guaiacol from o-anisidine by dissolving o-anisidine in iced water and sulphuric acid to form a solution, adding sodium nitrite to the thus formed solution for diazotization of the o-anisidine and then hydrolyzing the diazotized compound in a mixed liquid, at 135°–140° C., of conc. sulphuric acid and anhydrous sodium sulphate to obtain guaiacol. Further, Organic Synthesis, Collective Vol. 3, describes on page 130 thereof a process for the synthesis of 3-bromo-4-hydroxytoluene by diazotizing and hydrolyzing 3-bromo-4-aminotoluene; in this case a hydrolyzing temperature of 130°–135° C. is employed and a possible high temperature is generally believed to be desirable and, to this end, the hydrolyzing temperature is raised by the addition of sodium sulphate or the like.

Even if said diazotization and hydrolysis of o-anisidine be applied to a process for the production of p-hydroxybenzaldehyde from p-aminobenzaldehyde, p-hydroxybenzaldehyde will be obtained in a very low yield. Further, even if the process described in the aforesaid Organic Synthesis be applied to a process for the production of p-hydroxybenzaldehyde, the reaction will not satisfactorily proceed while producing tarry materials with the result that the desired product is obtained in a low yield as indicated in Comparative example 3 to be described later.

P-aminobenzaldehyde which may be used as a starting material for p-hydroxybenzaldehyde, is a compound which is thermally unstable in an acidic medium. It is easily condensed to form a Schiff's base as indicated in the following reaction formula:

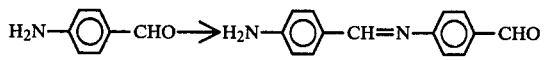

The condensation further proceeds to form the following polymer:

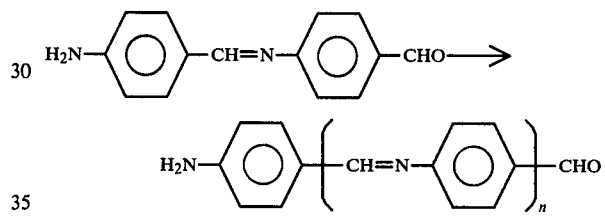

wherein n is an integer of one or more.

Thus, it is necessary to stabilize p-aminobenzaldehyde by converting it rapidly to its sulphate

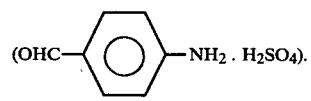

Various studies were made by the present inventors in an attempt to produce p-hydroxybenzaldehyde through p-aminobenzaldehyde from p-nitrotoluene and, as the result of their studies, it has been found that p-hydroxybenzaldehyde may be obtained in a good yield by dissolving p-nitrotoluene in a mixed solvent of an alcohol and an aqueous alkali solution, reacting the p-nitrotoluene in solution with sodium polysulphide in the presence or absence of an aprotic polar compound to produce p-aminobenzaldehyde, diazotizing the thus produced p-aminobenzaldehyde and then hydrolyzing the diazotized compound to obtain p-hydroxybenzaldehyde in a good yield. This invention is based on this finding or discovery.

An object of this invention is to provide a process for producing p-aminobenzaldehyde in a good yield from p-nitrotoluene. This process comprises reacting p-nitrotoluene with sodium polysulphide ($Na_2S_x$) prepared by reacting sodium hydroxide with hydrogen sulphide to form sodium hydrosulphide and incorporating the thus formed sodium hydrosulphide with sodium hydroxide and then with sulphur.

Another object of this invention is to provide a process for producing p-hydroxybenzaldehyde stably, substantially stoichiometrically and without producing tarry materials at the time of hydrolysis, from p-aminobenzaldehyde which is thermally unstable in an acidic medium. As means for attaining this object, intensive studies were made by the present inventors to find the optimum reaction time and temperature used in the conversion of p-aminobenzaldehyde to the sulphate thereof by the addition of sulphuric acid and also to find the optimum temperature range used in the hydrolysis of the diazonium salt when producing p-hydroxybenzaldehyde from p-aminobenzaldehyde, after which the optimum reaction conditions have been found. Thus, this process comprises adding p-aminobenzaldehyde to an aqueous solution (preferably 2–50 wt.%) of sulphuric acid at a specified temperature of 60°–100° C., preferably 75°–90° C., to form the sulphate thereof as rapidly as possible and hydrolyzing, after cooling, the thus formed sulphate with water or an aqueous solution (preferably, less than 70 wt.% concentration) of sulphuric acid at a specified temperature of 70°–100° C. to obtain p-hydroxybenzaldehyde under the advantageous conditions as mentioned above.

Still another object of this invention is to provide a novel process for producing p-hydroxybenzaldehyde through p-aminobenzaldehyde from p-nitrotoluene. This process comprises reacting p-nitrotoluene with sodium polysulphide prepared by reacting sodium hydroxide with hydrogen sulphide and incorporating the resulting sodium hydrosulphide with sodium hydroxide and then with sulphur, in the presence or absence of an aprotic polar compound in a mixed solvent consisting of an alcohol and an aqueous alkali solution to produce p-aminobenzaldehyde, adding the thus produced p-aminobenzaldehyde to an aqueous solution, preferably a 2–50 wt.% aqueous solution of sulphuric acid at 60°–100° C., preferably 75°–90° C., to produce the sulphate thereof rapidly, diazotizing (after cooling) the thus produced sulphate to obtain a diazonium salt of p-aminobenzaldehyde and then hydrolyzing the thus obtained diazonium salt in water or an aqueous solution of sulphuric acid at 70°–100° C. to obtain p-hydroxybenzaldehyde.

In producing p-aminobenzaldehyde by reacting p-nitrotoluene with sodium polysulphide according to this invention, the sodium polysulphide may preferably be a specific one which is prepared by reacting sodium hydroxide in aqueous solution with hydrogen sulphide to produce sodium hydrosulphide, adding sodium hydroxide to the thus produced sodium hydrosulphide to produce sodium sulphide and then adding sulphur to the sodium sulphide so produced, however, the sodium polysulphide does not have to be limited to the aforesaid specific one. It is preferable that the alcohol and the aqueous alkali solution be present in a ratio by weight of 0.1–2:1 in said mixed solvent, that the aqueous alkali solution contains an alkali in a concentration of 1–50% by weight thereof and that the mixed solvent be used in an amount of 4–100 parts by weight per part by weight of p-nitrotoluene. The concentration of the aqueous solution of sodium hydroxide to be reacted hydrogen sulphide is preferably in the range of 1–30% by weight. In the production of p-aminobenzaldehyde, it is preferable that p-nitrotoluene be reacted with sodium polysulphide in a molar ratio of 2–8:1 at a temperature of 50°–120° C. for a time sufficient to produce p-aminobenzaldehyde.

Even if sodium polysulphide prepared by a conventional known method is reacted with p-nitrotoluene in the production of p-aminobenzaldehyde from p-nitrotoluene, the p-aminobenzaldehyde will be produced in a remarkably increased yield so long as the reaction is effected in the presence of an aprotic polar compound in an "alcohol-alkali aqueous solution" mixed solvent according to this invention. Alternatively, the use of the specific sodium polysulphide according to this invention will result in producing p-aminobenzaldehyde in an increased yield even if the aprotic polar compound is not used in the reaction.

The alcohols which may be used in this invention include methanol, ethanol, ethylene glycol, ethylene glycol monomethyl ether, ethylene glycol monoethyl ether and mixtures thereof, among which alcoholic mixtures containing at least 80% by weight of ethanol (with the remainder being another alcohol, water or the like, or a mixture thereof) are preferred for increasing the yield of p-aminobenzaldehyde to be obtained.

The aprotic polar compounds used herein include N,N-dimethylformamide, N,N-diethylformamide, N,N-diphenylformamide, dimethylsulfoxide, tris(trimethylamino) phosphate, tetrahydrofuran, acetonitrile and other polar compounds which will not liberate $H^+$ therefrom. The use of the aprotic polar compound in an amount of 0.01–10% by weight of p-nitrotoluene will result in producing p-aminobenzaldehyde in a remarkably increased yield. The use thereof in an amount of less than 0.01% by weight will be ineffective in increasing the yield and the use thereof in amount of more than 10% by weight will, far from increasing the yield, decrease it. Among said aprotic polar compounds, N,N-dimethylformamide is particularly preferred.

It is unexpected that the reaction of the specific sodium polysulphide prepared by the previously mentioned new method different from conventional ones, with p-nitrotoluene will produce p-aminobenzaldehyde in a much higher yield (such as 55–60%) than has heretofore been possible. Although the mechanism of reaction between p-nitrotoluene and the specific sodium polysulphide is not clearly known, said much higher yield is considered to be due to delicate differences in chemical structure between the specified sodium polysulphide according to this invention and the conventional one.

The temperature at which hydrogen sulphide is reacted with sodium hydroxide in aqueous solution is not particularly limited, but it may preferably be a comparatively low temperature which is in the range of 10°–60° C. The use of lower temperatures will make the reaction prolonged, while the use of higher temperatures will decrease the reaction efficiency of the hydrogen sulphide.

It is desirable that sodium hydroxide be added to the sodium hydrosulphide obtained in a molar ratio of from 1.0 to 3.0 to produce sodium sulphide. The addition of sodium hydroxide in a molar ratio of less than 1.0 will result in producing p-aminobenzaldehyde in a low yield, while the addition thereof in a molar ratio of more than 3.0 will not result in increasing the yield to an appreciable extent, this being economically disadvantageous.

In the production of sodium polysulphide according to this invention by the addition of sulphur, it is desirable that sulphur be added in such an amount as to produce a sodium polysulphide represented by the formula $Na_2S_x$ wherein x is an integer of from 2 to 5. If sulphur be not added in such an amount as mentioned above, then by-products will be produced in large amounts and the desired product obtained in a decreased yield.

If the thus obtained sodium polysulphide according to this invention is reacted with p-nitrotoluene in a mixed solvent consisting of an aqueous alkali solution and an alcoholic mixture containing at least 80% by weight of ethanol, then p-aminobenzaldehyde will be obtained in a good yield.

According to this invention, it is necessary to react p-aminobenzaldehyde with sulphuric acid to form the sulphate thereof in as short a time as possible by heating said starting reactants to 60°–100° C. If p-hydroxybenzaldehyde be attempted to be obtained from the sulphate of p-aminobenzaldehyde, whether the reaction for producing the sulphate of p-aminobenzaldehyde was effected at lower than 60° C. for a long time or at higher than 100° C. for an extremely short time, the sulphate of p-aminobenzaldehyde obtained at the lower reaction temperature will give p-hydroxybenzaldehyde in a low yield while that obtained at the higher reaction temperature will disadvantageously give a low yield, accompanied with the formation of tarry materials.

Thus, according to this invention, a sulphuric acid solution and p-aminobenzaldehyde added thereto are reacted together at 60°–100° C., preferably 75°–90° C., under agitation for 10–30 minutes. The sulphuric acid concentration of the solution is not particularly limited, but it is preferably in the range of usually 2–50% by weight.

The sulphate of p-aminobenzaldehyde so obtained is immediately cooled (to a low temperature such as 10° to 0° C.) by cooled or iced water and then diazotized with a usual diazotizing agent such as an aqueous solution of sodium nitrite while adding the agent dropwise to the sulphate so cooled. It is effective or preferable in this case to add to the thus diazotized compound a decomposing agent, such as sulfamic acid or urea, in such an amount necessary for decomposing an excess of the sodium nitrite added. The diazotizing agents used herein may include sodium nitrite, potassium nitrite, ammonium nitrite and nitrosyl sulphuric acid, and they may be used in a concentration of 5–50% by weight at lower than 10° C. in the diazotization.

The diazonium salt of p-aminobenzaldehyde may preferably be hydrolyzed at a temperature in the range of from 70° to 100° C.; if the hydrolysis be effected at a temperature above 100° C. then tarry materials will be produced, while if it be effected at a temperature below 70° C. then it will not proceed smoothly. Therefore, it is necessary in the practice of this invention to carry out the hydrolysis at a temperature ranging from 70° to 100° C. in water or an aqueous solution of sulphuric acid.

This invention will be better understood by the following Examples and Comparative examples wherein all the percentages are by weight unless otherwise specified.

EXAMPLE 1

A solution of 5 g (0.125 mol) of sodium hydroxide in 10 g of water was introduced into a 100-ml flask, maintained at 45° C. and then reacted with 4.1 g (0.121 mol) of hydrogen sulphide by passing it through the solution for one hour, to obtain an aqueous solution of sodium hydrosulphide. The aqueous solution of sodium hydrosulphide so obtained was introduced into a 1-liter flask and incorporated with 9.1 g (0.228 mol) of sodium hydroxide and 547 g of water to produce an aqueous solution of sodium sulphide. The aqueous solution of sodium sulphide so produced was incorporated with 14.5 g (0.45 mol) and reacted together at 80° C. for one hour to produce an aqueous solution of sodium polysulphide which was represented by the formula $Na_2S_x$ wherein x is a value of 3.

To a 1-liter flask were added 66.7 g (0.487 mol) of p-nitrotoluene, 223 g of ethanol and 2.7 g (4.1% by weight of the p-nitrotoluene) of N, N-dimethylformamide to form a mixture which was dissolved, maintained at 80° C. and then incorporated dropwise over a period of time of 2 hours with an aqueous alkali solution prepared by adding 51.5 g of a 50% aqueous solution of sodium hydroxide to said aqueous solution of sodium polysulphide. After the end of the incorporation with the aqueous alkali solution, the whole mass was refluxed for an additional two hours thereby completing the reaction. The resulting reaction mixture was subjected to steam distillation to obtain 42.3 g (0.350 mol) of p-aminobenzaldehyde in purified form. The yield of the p-aminobenzaldehyde so obtained was 71.8%, based on the weight of p-nitrotoluene used.

To the same 1-liter flask as above were added 292.5 g of a 40% aqueous solution of sulphuric acid and 42.3 g (0.350 mol) of p-aminobenzaldehyde to form a mixture which was heated to 80° C., reacted at this temperature under agitation for 15 minutes, soon thereafter incorporated with 158.6 g of iced water to cool the resulting reaction mixture. The reaction mixture so cooled was incorporated dropwise over a time period of 30 minutes with a solution of 28.2 g (0.41 mol) of sodium nitrite in 79.3 g of water while maintaining the solution at a temperature of lower than 5° C., incorporated with 2.6 g (0.06 mol) of urea to decompose an excess of the sodium nitrite used and further incorporated with 529 g of iced water for dilution thereby obtaining 1132 g of an aqueous solution of a diazonium salt of p-aminobenzaldehyde.

The thus obtained aqueous solution of the diazonium salt maintained at lower than 5° C. was added dropwise over a period of time of 30 minutes to 767 g of a 20% aqueous solution of sulphuric acid heated to 80° C. and, soon after the end of the addition, heated rapidly to 90° C. to complete the hydrolysis of the diazonium salt thereby obtaining 43.2 g (0.354 mol) of p-hydroxybenzaldehyde. The yield of the thus obtained p-hydroxybenzaldehyde was substantially stoichiometric with respect to the amount of p-aminobenzaldehyde used and was therefore 71.8%, based on the weight of p-nitrotoluene used.

EXAMPLE 2

The procedure of Example 1 was followed except that 2.3 g (3.4 wt.% of the p-nitrotoluene) of acetonitrile were substituted for the N, N-dimethylformamide, to obtain 37.7 g (0.312 mol) of p-aminobenzaldehyde and then obtain 38.5 g (0.315 mol) of p-hydroxybenzaldehyde.

Thus, the yield of the thus obtained p-hydroxyaldehyde was 64.8%, based on the weight of p-nitrotoluene used.

EXAMPLE 3

The procedure of Example 1 was followed except that 3.2 g (4.8% by weight of the p-nitrotoluene) of dimethylsulfoxide were substituted for the N,N-dimethylformamide, to obtain 38.3 g (0.317 mol) of p- aminobenzaldehyde and then 39.1 g (0.320 mol) of p-hydroxybenzaldehyde. Thus, the yield of the p-hydroxybenzaldehyde was 65.8%, based on the weight of p-nitrotoluene used.

EXAMPLE 4

Thirty grams (0.125 mol) of sodium sulphide nonahydrate were dissolved in 600 g of water, incorporated with 15 g (0.47 mol) of sulphur, reacted together at 80° C. for one hour to produce sodium polysulphide, and then incorporated with 27 g of sodium hydroxide to form an aqueous alkali solution. The aqueous alkali solution so formed was added dropwise over a period of time of 2 hours to a solution of 50 g (0.36 mol) of p-nitrotoluene in a mixture of 232 g of ethanol and 4.2 g (8.4% by weight of the p-nitrotoluene) of N,N-dimethylformamide while maintaining said solution at 82° C. After the end of addition of the aqueous alkali solution, the whole mass was refluxed for an additional two hours to complete the reaction thereby producing p-aminobenzaldehyde. The amount of the p-aminobenzaldehyde so produced was 27.9 g (0.23 mol) and the yield thereof was 64%, based on the weight of p-nitrotoluene used. The p-aminobenzaldehyde so produced was diazotized and hydrolyzed in the same manner as in Example 1 to obtain 28.9 g (0.23 mol) of p-hydroxybenzaldehyde. The yield of this final product was 64%, based on the weight of p-nitrotoluene used.

COMPARATIVE EXAMPLE 1

The procedure of Example 1 was followed except that the N, N-dimethylformamide was not added, to obtain p-hydroxybenzaldehyde. The yield of the p-hydroxybenzaldehyde was 56%, based on the weight of p-nitrotoluene used.

COMPARATIVE EXAMPLE 2

The procedure of Example 4 was followed except that the N, N-dimethylformamide was not added, to obtain p-hydroxybenzaldehyde in a yield of 40%, based on the weight of p-nitrotoluene used.

COMPARATIVE EXAMPLE 3

The procedure of Example 1 was repeated except that the N,N-dimethylformamide was not added and p-aminobenzaldehyde was reacted with sulphuric acid in 40% aqueous solution at 40° C. for one hour, to obtain p-hydroxybenzaldehyde in a yield of 23%, based on the weight of p-nitrotoluene used.

EXAMPLE 5

A solution of 14 g (0.35 mol) of sodium hydroxide in 28 g of water was introduced into a 100-ml flask where the solution was maintained at 45° C. and reacted with 10.6 g (0.31 mol) of hydrogen sulphide by passing it through said solution for one hour to obtain 52.6 g of an aqueous solution of sodium hydrosulphide. The sodium hydrosulphide solution so obtained was introduced into a 2-liter flask where it was incorporated with 22 g (0.55 mol) of sodium hydroxide and 1435 g of water to obtain 1509.6 g of an aqueous solution of sodium sulphide. The aqueous solution of sodium sulphide so obtained was incorporated with 37.4 g (1.17 mol) of sulphur to react the sulphide with sulphur at 80° C. for one hour thereby obtaining 1547 g of an aqueous solution of sodium polysulphide which could be represented by the formula $Na_2S_x$ wherein x is 3.29. The aqueous solution of sodium polysulphide so obtained was incorporated with 135 g of a 50% aqueous solution of sodium hydroxide to render the former alkaline.

A solution of 175 g (1.28 mol) of p-nitrotoluene in 590 g of ethanol was charged into a 3-liter flask, maintained at 82° C. and then incorporated dropwise with the whole of said alkaline aqueous solution of sodium polysulphide over a period of time of two hours, after which the whole mass was refluxed for another two hours to complete the reaction. The reaction mixture so obtained was analyzed by high-speed liquid chromatography and found to comprise 87.4 g (0.72 mol) of p-aminobenzaldehyde and 9.6 g (0.090 mol) of p-toluidine. The reaction mixture was subjected to steam distillation to distil off the ethanol and p-toluidine, and the p-aminobenzaldehyde was crystallized and filtered out to obtain 86 g (0.71 mol) of p-aminobenzaldehyde in crystal form. The yield of p-aminobenzaldehyde so obtained was 56%, based on the weight of p-nitrotoluene obtained.

EXAMPLE 6

The procedure of Example 5 was followed except that 23.5 g (0.59 mol) of sodium hydrosulphide were added to the aqueous solution of sodium hydrosulphide obtained, to obtain 92.9 g (0.77 mol) of p-aminobenzaldehyde in a yield of 60% of p-nitrotoluene used.

EXAMPLE 7

The procedure of Example 6 was followed except that a modified ethanol containing 10% of methanol was substituted for the ethanol, to obtain 88.3 g (0.73 mol) of p-aminobenzaldehyde. The yield of p-aminobenzaldehyde so obtained was 57%, based on the weight of p-nitrotoluene used.

COMPARATIVE EXAMPLE 4 (the method as described in the previously mentioned Organic Synthesis)

A solution of 30 g (0.125 mol) of sodium sulphide nonahydrate in 600 g of water was introduced into a 1-liter flask, incorporated with 15 g (0.47 mol) of sulphur and reacted therewith at 80° C. for one hour to obtain sodium polysulphide in aqueous solution. This sodium polysulphide was such that it was represented by the formula $Na_2S_x$ wherein x was 4.5. The sodium polysulphide in aqueous solution so obtained was incorporated with 27 g of sodium hydroxide to obtain an alkaline aqueous solution which was added dropwise at 82° C. to a solution of 50 g (0.36 mol) of p-nitrotoluene in 300 ml of 95% ethanol (the remaining 5% being substantially methanol) over a period of time of 2 hours, after which the whole mass was refluxed for 2 hours to complete the reaction. The reaction mixture thus obtained was subjected to high-speed liquid chromatography and found to contain 18.3 g (0.15 mol) of p-aminobenzaldehyde and 3.9 g (0.036 mol) of p-toluidine.

The reaction mixture was subjected to steam distillation to distil off the ethanol and the p-toluidine, and then the p-aminobenzaldehyde was crystallized and filtered out thereby obtaining 17.4 g (0.14 mol) of crystals thereof. The yield of p-amonibenzaldehyde so obtained was 40%, based on the weight of p-nitrotoluene used.

COMPARATIVE EXAMPLE 5

The procedure of Example 5 was followed except that 8 g (0.2 mol) of sodium hydroxide were added to the 52.6 g of the aqueous solution of sodium hydrosulphide, to obtain 69.7 g (0.576 mol) of p-aminobenzaldehyde which was represented by the formula Na$_2$S$_x$ wherein x is 5.38.

The yield of p-aminobenzaldehyde so obtained was 45%, based on the weight of p-nitrotoluene used.

EXAMPLE 8

To a 500-ml glass-made reactor provided with an agitator were added 33.2 g of a 40% aqueous solution of sulphuric acid and 4.8 g (0.04 mol) of p-aminobenzaldehyde to form a mixture. The mixture so formed was heated to 80° C., reacted together under agitation at this temperature for 15 minutes, incorporated with 18 g of iced water to cool the resulting reaction mixture rapidly, incorporated dropwise over a time period of 30 minutes with a solution of 3.2 g (0.047 mol) of sodium nitrite in 9 g of water while maintaining the solution at a temperature below 5° C., incorporated with 0.3 g (0.005 mol) of urea to decompose an excess of the sodium nitrite and then incorporated with 60 g of iced water for dilution thereby to obtain 128.5 g of an aqueous solution of a diazonium salt of p-aminobenzaldehyde.

The thus obtained diazonium salt solution maintained at a temperature below 5° C. was added over a period of time of 30 minutes to 87 g of a 20% aqueous solution of sulphuric acid heated to 80° C., after which the whole mass was heated rapidly to 90° C. to complete the hydrolysis of the diazonium salt. The thus obtained p-hydroxybenzaldehyde amounted to 4.9 g (0.04 mol) and the yield thereof was substantially stoichiometric with respect of the amount of p-aminobenzaldehyde used.

EXAMPLE 9

The procedure of Example 8 was followed except that 87 g of water were used in substitution for the 20% aqueous solution of sulphuric acid as the decomposing liquid, to obtain 4.5 g (0.037 mol) of p-hydroxybenzaldehyde. The yield thereof was 92%, based on the weight of p-aminobenzaldehyde used.

COMPARATIVE EXAMPLE 6

The procedure of Example 8 was followed except that the production of the sulphate of p-aminobenzaldehyde by reaction with sulphuric acid in 40% aqueous solution was effected at 40° C. for one hour, to obtain 2.0 g (0.016 mol) of p-hydroxybenzaldehyde. The yield thereof was 41%, based on the weight of p-aminobenzaldehyde used.

COMPARATIVE EXAMPLE 7

The procedure of Example 8 was followed except that the reaction of p-aminobenzaldehyde with sulphuric acid in 40% aqueous solution was effected at 120° C. for 15 minutes, to obtain 2.6 g (0.021 mol) of p-hydroxybenzaldehyde, accompanied with formation of tarry materials in large quantities. The yield of p-hydroxybenzaldehyde so obtained was 53%, based on the weight of p-aminobenzaldehyde used.

COMPARATIVE EXAMPLE 8

The procedure of Example 8 was followed except that a mixture of 15 g of sodium sulphate with 30 g of a 67% aqueous solution of sulphuric acid was substituted for the 20% aqueous solution of sulphuric acid as the decomposing liquid and that a hydrolyzing temperature of 130° C. was used, to obtain 2.0 g (0.016 mol) of p-hydroxybenzaldehyde. The yield of p-hydroxybenzaldehyde so obtained was 42%, based on the weight of p-aminobenzaldehyde, and, in this case, tarry materials were produced in large quantities.

What is claimed is:

1. In a process for producing p-aminobenzaldehyde from p-nitrotoluene comprising reacting p-nitrotoluene with sodium polysulphide in a mixed solvent consisting of at least one alcohol and an alkali aqueous solution in the presence of an aprotic polar compound to produce the p-aminobenzaldehyde.

2. A process according to claim 1, wherein the at least one alcohol is a member selected from the group consisting of methanol, ethanol, ethylene glycol, ethylene glycol monomethyl ether, ethylene glycol monoethyl ether and mixtures thereof.

3. A process according to claim 1, wherein the at least one alcohol contains at least 80% by weight of ethanol.

4. A process according to claim 1, wherein the aprotic polar compound is used in an amount of 0.01–10% by weight of p-nitrotoluene.

5. A process according to claim 1, wherein the aprotic polar compound is a member selected from the group consisting of N,N-dimethylformamide, N,N-diethylformamide, N,N-diphenylformamide, dimethylsulfoxide, tris(trimethylamino)phosphate, tetrahydrofuran and acetonitrile.

6. A process according to claim 1, wherein the sodium polysulphide is represented by the formula Na$_2$S$_x$ wherein x is an integer of 2–5.

7. A process according to claim 5, wherein the sodium polysulphide is represented by the formula Na$_2$S$_x$ wherein x is an integer of 2–5.

8. A process according to claim 1, wherein the sodium polysulphide is one prepared by reacting sodium hydroxide in aqueous solution with hydrogen sulphide to produce sodium hydrosulphide, reacting the thus produced sodium hydrosulphide with sodium hydroxide to produce sodium sulphide and then reacting the thus produced sodium sulphide with sulphur to produce the sodium polysulphide.

9. A process according to claim 8, wherein the reaction of sodium hydroxide in aqueous solution with hydrogen sulphide is effected at a temperature of 10°–60° C.

10. A process according to claim 8, wherein the sodium hydrosulphide is incorporated with the sodium hydroxide in a molar ratio of 1.0–3.0.

11. A process for producing a diazonium salt of p-aminobenzaldehyde from p-nitrotoluene comprising the steps of:
reacting p-nitrotoluene with sodium polysulphide in a mixed solvent consisting of at least one alcohol and an alkali aqueous solution in the presence of an aprotic polar compound to produce p-aminobenzaldehyde,
adding the thus produced p-aminobenzaldehyde to an aqueous solution of sulphuric acid at 60°–100° C. to produce the sulphate thereof rapidly, and
diazotizing, after cooling, the thus produced sulphate to produce a diazonium salt of p-aminobenzaldehyde.

12. A process according to claim 11, wherein the aqueous solution of sulphuric acid contains sulphuric acid in a concentration of 2–50% by weight of the solution.

* * * * *